United States Patent [19]
Campbell, Jr.

[11] Patent Number: 5,030,235
[45] Date of Patent: Jul. 9, 1991

[54] PROSTHETIC FIRST RIB

[76] Inventor: Robert M. Campbell, Jr., 7940 Floyd Curl Dr., Ste. 630, San Antonio, Tex. 78229

[21] Appl. No.: 512,646

[22] Filed: Apr. 20, 1990

[51] Int. Cl.$^5$ .............................................. A61F 2/28
[52] U.S. Cl. ........................................ 623/16; 623/19
[58] Field of Search ..................................... 623/16-19; 606/60, 69-71; 128/69

[56] References Cited

U.S. PATENT DOCUMENTS 4,327,715 5/1982 Corvisier ............................... 623/16

FOREIGN PATENT DOCUMENTS 0610518 6/1978 U.S.S.R. ............................... 606/71

Primary Examiner—Ronald Frinks
Attorney, Agent, or Firm—Gunn, Lee & Miller

[57] ABSTRACT

Applicant's invention is a prosthetic rib for attachment between a patient's scapula and clavicle. The prosthetic rib serves to provide a generally anterior/posteriorly oriented platform to which other prostheses otherwise attachable a natural rib near the same position would be attached. The prosthetic rib includes a clavicle carriage for attachment to the clavicle, a scapula carriage for attachment to the scapula and a rib sleeve which intervenes the clavicle and scapula carriages and is the platform to which other prostheses may be attached.

1 Claim, 4 Drawing Sheets

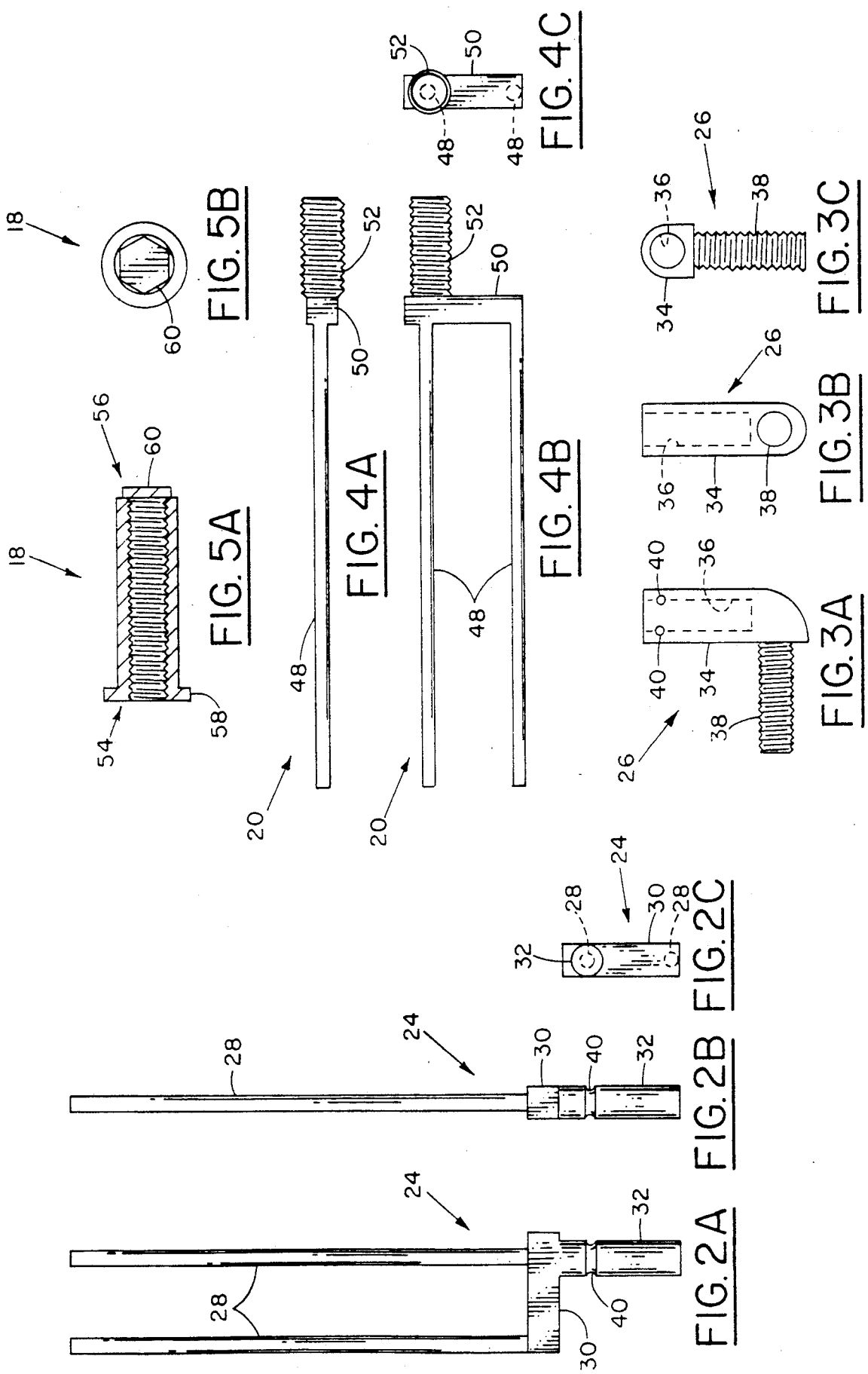

PROSTHETIC FIRST RIB

BACKGROUND OF THE INVENTION

1. Field of the Invention

Applicant's invention relates to prosthetic replacement and augmentation of skeletal components or therapeutic manipulations of deformities thereof.

2. Background Information

Applicant herein is the inventor of a vertical prosthetic rib which is the subject of two patent applications now pending before the United States Patent & Trademark Office—Ser. No. 07/338,227 filed 04/14/89 and a continuation-in-part application filed on 04/13/90 as a PCT application, International Application No. PCT/US90/02018. The disclosure contained in the aforementioned patent applications is incorporated herein by reference.

The vertical prosthetic rib of applicant's invention as claimed in the aforementioned two patent applications ordinarily requires at least two natural ribs to which the vertical prosthetic rib may be anchored. Furthermore, one of these two natural ribs must be superior to the thoracic region to be spanned by the vertical prosthetic rib and the other must be inferior thereto.

There are occasions where no natural rib is available at the desired superior termination point of the vertical prosthetic rib. There may be no natural rib in that position at all, or the natural rib(s) in that area may be damaged or congenitally too unstable to serve as a suitable support for the vertical prosthetic rib.

In a number of occasions known to Applicant, the vertical prosthetic rib is virtually the only practical life-saving means available to address a profound chest wall defect and yet there is no natural rib in the superior position. In these situations, the lack of any superior anchor site for the vertical prosthetic rib may translate to death of the patient.

SUMMARY OF THE INVENTION

It is an object of the present invention to provide a novel prosthetic first rib to which a vertical prosthetic rib may be attached in the superior termination point of the intended span of the vertical prosthetic rib.

It is another object of the present invention to provide a prosthesis which serves as a first rib and which may serve an attachment platform for other prostheses or natural anatomical constituents.

In satisfaction of these and related objectives, applicant's present invention provides a prosthetic first rib which is attachable to the clavicle at a first end and to the scapula on the corresponding anatomical side of the patient. Applicant's invention, once implanted, permits its practitioner to attach protheses thereto which otherwise would be attached to the first natural rib or a natural rib in close proximity thereto.

BRIEF DESCRIPTION OF THE DRAWINGS

FIG. 2a is a side elevational view of the clavicle carriage rod unit of applicant's invention.

FIG. 2b is a top plan view of the clavicle carriage rod unit of applicant's invention.

FIG. 2c is an end view of the clavicle carriage rod unit of applicant's invention.

FIG. 3a is a side elevational view of the clavicle carriage sleeve of applicant's invention.

FIG. 3b is an end view of the clavicle carriage sleeve of applicant's invention.

FIG. 3c is a top plan view of the clavicle carriage sleeve of applicant's invention.

FIG. 4a is a top plan view of the scapula carriage of applicant's invention.

FIG. 4b is a side elevational view of the scapula carriage of applicant's invention.

FIG. 4c is an end view of the scapula carriage of applicant's invention.

FIG. 5a is a top plan view of the rib sleeve of applicant's invention.

FIG. 5b is an elevational view of the rib sleeve of applicant's invention.

DETAILED DESCRIPTION OF THE PREFERRED EMBODIMENT

Figure 1:
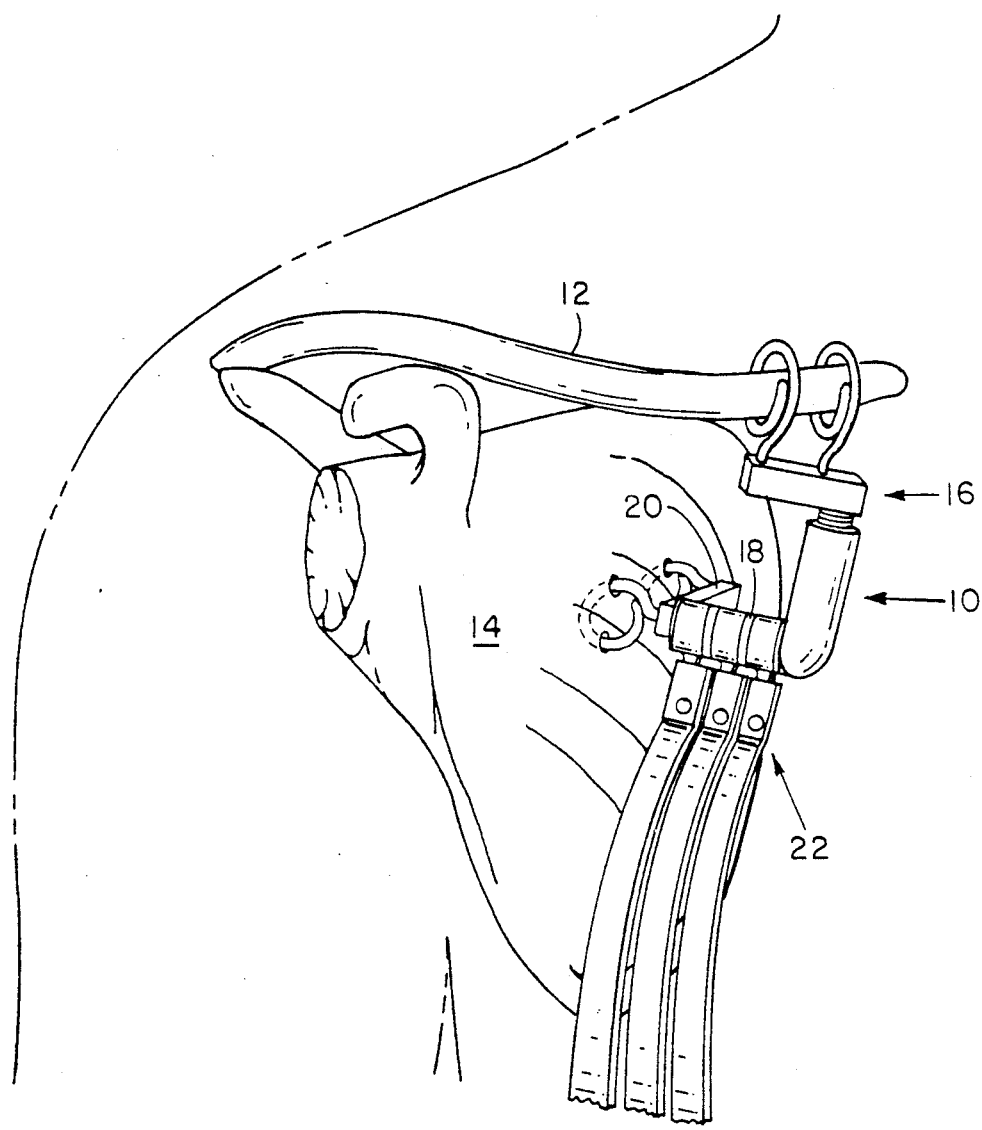
FIG. 1 is a perspective view of the preferred embodiment implanted in a patient.

Referring to FIG. 1, the device of applicant's invention herein (hereinafter referred to as "the prosthetic first rib 10") is depicted as being implanted in the right anatomical side of a patient. The device is identified generally by the reference number 10.

The overall, orientation of the prosthetic first rib 10 is generally anterior/posterior. The prosthetic first rib 10 is attached in the anterior position to the patient's clavicle 12 as shown. The prosthetic first rib 10 is attached in the posterior position to the patient's scapula 14.

Still referring principally to FIG. 1, the prosthetic first rib 10 itself includes three principal component subsystems: the clavicle carriage 16, the rib sleeve 18 and the scapula carriage 20. Associated therewith, and part of applicant's invention are the prosthetic rib carriers 22.

Referring principally to FIGS. 2a, 2b, 2c, 3a, 3b and 3c, the clavicle carriage 16 includes two primary subcomponents—a clavicle carriage rod unit 24 and a clavicle carriage sleeve 26. The clavicle carriage rod unit 24 includes two clavicle rods 28 which, like "rods 20" of applicant's vertical prosthetic rib as described in the above-referenced patent applications, are made from commercially pure titanium in the preferred embodiment. The diameter and length of the clavicle rods 28 may vary according to the patient to receive the prosthetic first rib 10. The clavicle rods 28 extend from a clavicle rod unit base block 30. The clavicle unit base block 30 includes a cylindrically-shaped clavicle unit shaft 32 extending from the side of the clavicle unit base block 30 opposite the clavicle rods 28 and in the opposite direction as shown.

The clavicle carriage sleeve 26 includes a clavicle shaft receptor 34 with a cylindrically-shaped hollow 36 opening at one end and sized for telescopically receiving the clavicle unit shaft 32 therein. A right-handed thread, threaded clavicle unit stud 38 extends from the clavicle shaft receptor 34 at an approximately 90° angle relative to the longitudinal orientation of the hollow 36.

The clavicle unit shaft 32 has a circumferential recess 40 which serves in conjunction with one or more cotter keys (not shown in the figures) which are correspondingly extended through one or more of holes 42 in the clavicle shaft receptor 34 to maintain the clavicle rod unit 24 and the clavicle carriage sleeve 26 in a mated configuration.

As is clear from the described configuration of the components of the clavicle carriage 16, the clavicle rod unit 24 may rotate relative to the clavicle carriage sleeve 26 to permit desired orientations for both components.

Referring principally to FIGS. 4a, 4b and 4c, the scapula carriage 20 includes two scapula rods 48 extending from a scapula rod unit base block 50 as shown. Like "rods-20" of applicant's vertical prosthetic rib as described in the above-referenced patent applications and clavicle rods 28, scapula rods 48 are made from commercially pure titanium. The diameter and length of the scapula rods 48 may vary according to the patient to receive the prosthetic first rib 10. A left-handed thread, threaded scapula unit stud 52 extends from the side of the scapula unit base block 50 opposite the scapula rods 48 and in the opposite direction as shown.

Referring principally to FIGS. 5a and 5b, the rib sleeve 18 is essentially a interiorly threaded cylinder with a scapula end 54 and a clavicle end 56 and open at both such ends. An annular flange 58 is formed at the scapula end 54 of the rib sleeve 18 and serves as an abutment past which a prosthetic rib carrier 22 cannot pass. A hex nut-shaped projection 60 is formed at the clavicle end 56 of the rib sleeve 18. The hex nut-shaped projection 60 facilitates rotation of the rib sleeve 18 (using a wrench) the purpose for which will be described in the next paragraph. The hex nut-shaped projection 60 is centrally open such that the channel through the rib sleeve 18 is not obstructed.

Figure 6A:
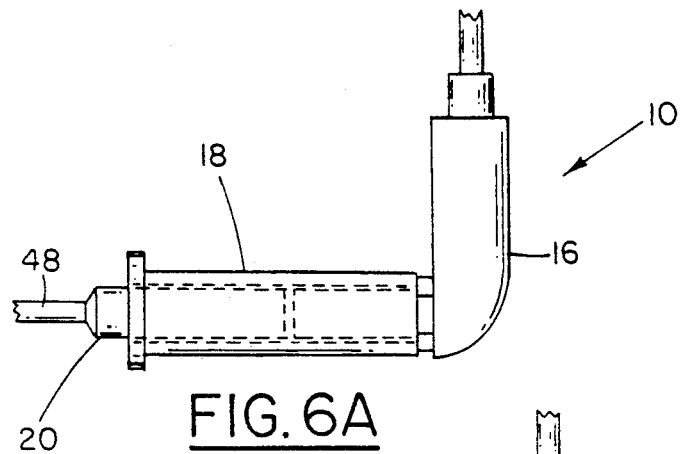
FIG. 6a is a side elevational view of a portion of the prosthetic first rib of applicant's invention indicating the adjustment thereof in the least extended configuration.
Figure 6B:
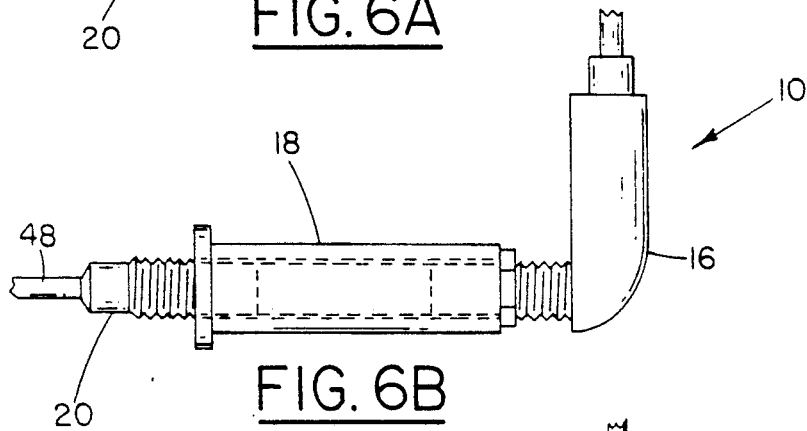
FIG. 6b is a side elevational view a portion of the prosthetic first rib of applicant's invention indicating the adjustment thereof to an extended configuration through rotation of the rib sleeve.
Figure 6C:
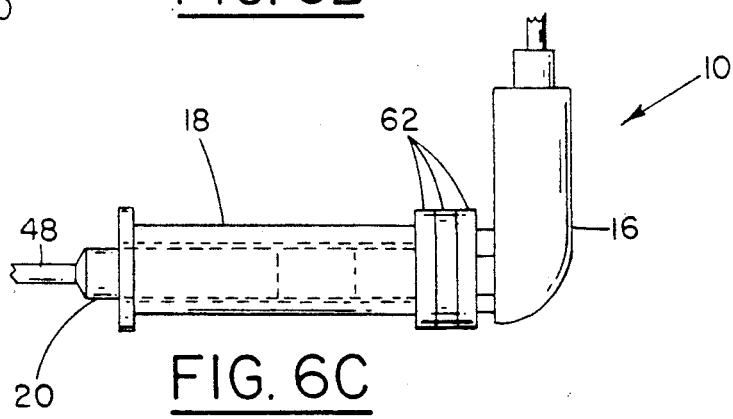
FIG. 6c is a side elevational view of FIG. 6b with the additional representation of the use of spacer(s) for covering exposed threads when the prosthetic first rib is in an extended configuration and for maintaining the prosthetic first rib in such extended configuration.
Figure 7:
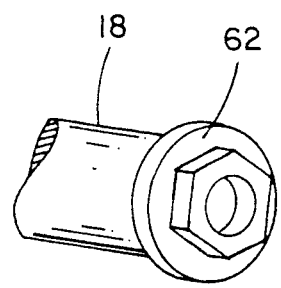
FIG. 7 is an end perspective view of the rib sleeve of applicant's invention with a spacer situated thereon.
Figure 7A:
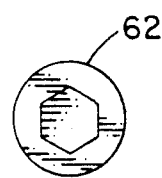
FIG. 7a includes a front elevational view of a spacer as depicted installed in FIG. 6c.
Figure 7B:
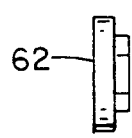
FIG. 7b includes a side elevational view of a spacer as depicted installed in FIG. 6c.
Figure 8A:
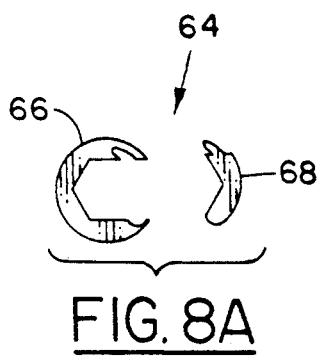
FIG. 8a is an exploded side elevational view of an auxiliary spacer for use with the prosthetic first rib of applicant's invention after initial implantation thereof.
Figure 8B:
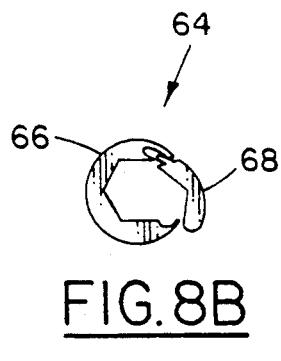
FIG. 8b is a side elevational view of an auxiliary spacer for use with the prosthetic first rib of applicant's invention after initial implantation thereof with the closure member partially situated in the implanted position relative to the spacer body.
Figure 8C:
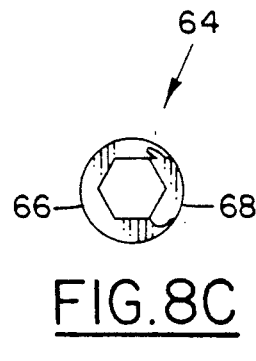
FIG. 8c is a side elevational view of an auxiliary spacer for use with the prosthetic first rib of applicant's invention after initial implantation thereof with the closure member completely situated in the implanted position relative to the spacer body.
Figure 8:
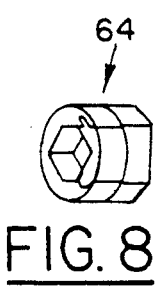
FIG. 8 is a perspective view of two adjacent auxiliary spacers for use with the prosthetic first rib of applicant's invention after initial implantation thereof.

Referring principally to FIGS. 6a, 6b and 6c, the rib sleeve 18 acts as a union nut for simultaneously retracting or extending the clavicle unit stud 38 and the scapula unit stud 52 relative to their respective ends of the rib sleeve 18. The purpose of this configuration is to permit attachment of the clavicle carriage 16 and the scapula carriage 20 to their respective sites prior to their joinder by way of the rib sleeve 18. Additionally, this configuration permits adjustment of the length of the prosthetic first rib 10 (as measured parallel with the longitudinal axis of the rib sleeve 18) by simply rotating the rib sleeve 18 in either direction.

Referring principally to FIGS. 6a, 6b, 7, 7a and 7b, one or more spacers 62 may be used at the clavicle end 56 of the rib sleeve 18 if the prosthetic first rib 10 is initially to be extended in a manner where a portion of the clavicle unit stud 52 remains outside of the rib sleeve 18. The spacers 62 are formed to mate (as the female portion of the pairing) on one side with the hex nut-shaped projection 60 of the rib sleeve 18 and to duplicate the hex nut-shaped projection 60 of the rib sleeve 18 on the other side. The diameter of the spacers 62 is substantially the same as the annular flange 58 at the scapula end 54 of the rib sleeve 18 and, when installed, serves the same essential purpose. Additionally, the spacer(s) 62 serve to provide substitute means for adjusting the rib sleeve 18 over the then-obstructed hex nut-shaped projection 60 of rib sleeve 18.

Referring to FIGS. 8, 8a, 8b and 8c, an auxiliary spacer 64 is designed for installation after implantation of the prosthetic first rib 10. As shown, the auxiliary spacer 64 has a removable segment 68 which permits the auxiliary spacer 64 be added to the prosthetic first rib 10 by passing the spacer body 66 over the clavicle unit stud 38 with the removable segment 68 being snapped into place thereafter. Like the spacer 62, one side of auxiliary spacer 64 has a female receptor for the hex nut-shaped projection 60 of the rib sleeve 18 and the other side is formed for duplicating the hex nut-shaped projection 60.

Figure 9:
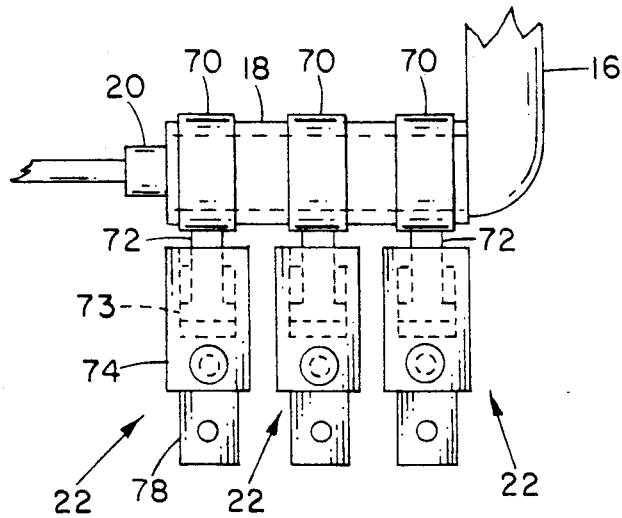
FIG. 9 is an elevational view of three rib carriages in place on the rib sleeve of applicant's invention.
Figures 10A, 10B:
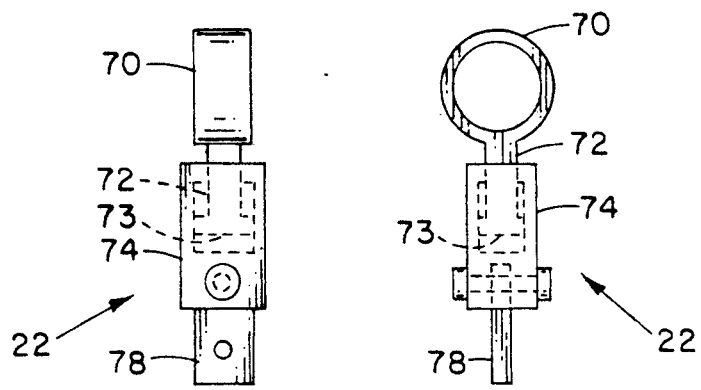
FIG. 10a is a side elevational view of a rib carriage of applicant's invention.
FIG. 10b is a front elevational view of a rib carriage of applicant's invention.

Referring to FIGS. 9, 10a and 10b, the prosthetic rib carriers 22 are designed to operably replace the "rib sleeve carriage attachments 14" of applicant's vertical prosthetic rib as described in the above-referenced patent applications by applicant herein.

Each prosthetic rib carrier 22 includes a cylindrically shaped rib carrier collar 70 with an interior diameter for telescopically, snugly receiving the rib sleeve 18 therethrough. Each rib carrier collar 70 includes a rib carrier piston 72 formed as an integral part thereof. The rib carrier piston 72 has an annular flange 73 formed at its distal end.

A rib carrier cylinder 74 with a cylindrically shaped rib carrier cylinder hollow 76 formed therein and open at one end telescopically receives the rib carrier piston 72 as shown in FIGS. 9 and 10. The rib carrier cylinder hollow 76 is of a diameter such that the annular flange 73 of the rib carrier piston 72 may be telescopically received therein. The exterior opening to the rib carrier cylinder hollow 76 is circular when viewed along the longitudinal, central axis of the rib carrier cylinder 74 and is narrowed relative to the over-all rib carrier cylinder hollow 76 such that it has a diameter less than that of the flange 73. In this manner, the rib carrier piston 72 cannot move from the hollow 76 once it is situated therein in the manufacturing process.

A rib sleeve projection 78 is pivotally attached to the rib carrier cylinder 74 on the opposite end from the exterior opening of the rib carrier cylinder hollow 76 as shown in FIGS. 9 and 10. The rib sleeve projection 78 serves the same function as the rib sleeve projection of applicant's previously mentioned vertical prosthetic rib (identified by the reference numeral "14a" in the aforementioned patent applications by applicant).

Because of the relative movement allowed by the piston/cylinder arrangement between the rib sleeve 18 and the rib carrier collar 70 as well as the pivotal arrangement between the rib carrier cylinder 74 and the rib sleeve projection 78, a vertical prosthetic rib attached to a prosthetic rib carrier 22 is allowed a significant range of motion. This allows the surgeon a certain degree of latitude in orienting the vertical prosthetic ribs to direct them to desired inferior attachment sites and thereby achieve the desired therapeutic objective. In addition, the piston/cylinder arrangement between the rib carrier cylinder 74 and the rib carrier piston 72 allows movement of the superior end of a vertical prosthetic rib attached to the rib carrier 22 in response to inwardly directed force on the vertical prosthetic rib. This, in turn, allows the vertical prosthetic rib to act as a "shock absorber" and thereby reduces the likelihood that the clavicle and/or the inferior natural rib to which the vertical prosthetic rib is attached will be fractured in any given accident.

Referring again to FIG. 1, the clavicle rods 28 are to circumvent the clavicle 12 in much the same manner as described for "rods 20" of applicant's vertical prosthetic rib.

Each of the scapula rods 48 are attached to the scapula 14 by through the scapula 14 through a first hole and back through the scapula through a second hole as shown in the drawing.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A device for implantation as a prosthetic rib comprising:
    a clavicle carriage for attachment to a clavicle of an intended recipient of said device;
    a scapula carriage for attachment to a scapula of said intended recipient of said device;
    a rib sleeve having first and second ends, said first end for connection to said clavicle carriage and said second end for connection to said scapula carriage; and
    a rib carriage connected with said rib sleeve.

* * * * *